United States Patent [19]

Lemperle

[11] Patent Number: 5,344,452
[45] Date of Patent: Sep. 6, 1994

[54] ALLOPLASTIC IMPLANT

[76] Inventor: Martin Lemperle, Röderbergweg 43, D-6000 Frankfurt 1, Fed. Rep. of Germany

[21] Appl. No.: 572,975
[22] PCT Filed: Dec. 8, 1989
[86] PCT No.: PCT/EP89/01508
 § 371 Date: Aug. 6, 1990
 § 102(e) Date: Aug. 6, 1990
[87] PCT Pub. No.: WO90/06093
 PCT Pub. Date: Jun. 14, 1990

[30] Foreign Application Priority Data

Dec. 8, 1988 [DE] Fed. Rep. of Germany ....... 3841401

[51] Int. Cl.$^5$ .............................................. A61F 2/02
[52] U.S. Cl. .......................................... 623/11; 623/4; 623/14
[58] Field of Search ................ 606/76, 77; 623/11, 623/12, 16, 18, 66

[56] References Cited

U.S. PATENT DOCUMENTS

| | | | |
|---|---|---|---|
| 3,223,083 | 12/1965 | Cobey | 606/76 |
| 3,882,858 | 5/1975 | Klemm | 606/76 |
| 4,197,846 | 4/1980 | Bucalo | 623/66 |
| 4,500,658 | 2/1985 | Fox | 523/117 |
| 4,547,390 | 10/1985 | Ashman et al. | 623/16 |
| 4,657,548 | 4/1987 | Nichols | 623/66 |
| 4,705,519 | 11/1987 | Hayes et al. | 623/16 |
| 4,718,910 | 1/1988 | Draenert | 623/16 |
| 4,786,555 | 11/1988 | Howard, Jr. | 623/11 |

FOREIGN PATENT DOCUMENTS

| | | | |
|---|---|---|---|
| 2287210 | 5/1976 | France | |
| 0629517 | 4/1982 | Switzerland | 623/16 |
| 8707495 | 12/1987 | World Int. Prop. O. | |

OTHER PUBLICATIONS

Krukowski, et al "Charged Beads Stimulate Bone Formation" 34th Annual Meeting Orth. Res. Soc. Feb. 1988.

*Primary Examiner*—David Isabella
*Attorney, Agent, or Firm*—Lowe, Price, LeBlanc & Becker

[57] ABSTRACT

Alloplastic implant based on a biocompatible solid in powder form, in particular a plastic. The solid particles have a smooth surface, free from corners and edges. The solid particles are preferably manufactured from poly(methyl methacrylate) (PMMA), preferably in the form of pellets. The alloplastic implant can be injected below the skin to even out irregularities of any origin; it remains permanently at the injection site and causes no side effects.

15 Claims, No Drawings

ALLOPLASTIC IMPLANT

DESCRIPTION

1. Technical Field

The invention relates to an alloplastic implant on the basis of a histocompatible solid. The implant is particularly used in to even out skin irregularities. It can, however, be used for any other purpose in plastic surgery.

2. Background Art

It has been tried to "restore" elements of the human body which are pathologically changed or accidentally destroyed. Where necessary, such elements are replaced by foreign bodies. In particular, in the area of the plastic surgery and cosmetic surgery, implants are used more and more.

It is very often desired to even out irregularities of the skin of any origin permanently and without side effects. Using different materials such as collagen for this purpose and of course also for other purposes in plastic surgery is known.

Collagen is a xenogeneic protein product which is degraded in the body. In case an irregularity of the skin has been evened out with collagen, for instance by an injection under the skin (intracutanously or subcutaneously) then it is normally necessary to have further injections in order to restore the results originally obtained after the first injection.

Furthermore collagen causes allergies so that allergic reactions can be observed in at least 3% of the cases. The likelihood of allergic reaction increases with multiple injections which is normally required to obtain the desired result.

It is furthermore known to use gelatine for the above given purpose. However, gelatine has similar drawbacks as collagen. In addition it is much more difficult to inject gelatine.

Also, silicone or silicone oils, respectively, have been used. However, silicone oils cause a severe reaction of the tissue at the site of the injection (siliconome). In addition, the silicone oils are rather badly kept in place by the tissue at the injection site so that, as a consequence, the silicone oils are transmitted to more or less distant parts of the body, for instance lymphatic nodules and liver.

It is also known to perform an injection of fat by using endogenous fat for the purposes mentioned above. It has been observed, however, that such a measure frequently causes infection. Furthermore the endogenous fat is rapidly and strongly absorbed by the body so that normally only 10% of the injected fat remain immobilised at the desired site.

DISCLOSURE OF INVENTION

It is therefore an object of the present invention to provide an alloplastic implant which can easily be injected, remains immobilised at the site where it has been injected and is tolerated by the tissue so that no side effects are caused.

According to the present invention a histocompatible solid in the form of a powder is used as an implant. The solid particles forming the solid, which may be incorporated into a suspending agent, are injected for instance with an injection needle at the desired site.

The solid particles used according to the present invention have a smooth surface and are free from corners, edges and so on. In other words, the particles are not allowed to have sharp transitions at their surface. Said transitions are for instance found at such corners and edges. In addition they are not allowed to have peaks of any kind or tapered projections. Furthermore the surface should not have pores.

Consequently the transition from one outer surface to the other outer surface of the solid particles as used according to the present invention has to take place in a continuous manner. If such transitions are present, as it is the case for the edges of a cube, they have to be smoothed off.

According to the present invention it is therefore not possible to use solid particles which are crystallitres (for instance needle-shaped) or particles which have been obtained by mechanically breaking up greater units into small pieces since said particles possess the above mentioned sharp edges and corners.

Due to the smooth and smoothed off surface structure no cells and other tissue structures are damaged. In addition the danger of causing reactions of the tissue, which are followed by infections, is minimised.

Preferably dynamically balanced solid particles and in particular particles having an elliptic or spherical form are used. In addition, it is possible to use solid particles of a different geometrical form if all the particles have a smooth and smoothed off surface.

The solid particles which are present as a dust or powder, respectively, possess preferably an average diameter of about $\geq 10$ $\mu$m. Such solid particles are too large to be "eaten" by monocytes. It is, however, also possible to use smaller solid particles in the range of 4 to 5 $\mu$m or 5 to 10 $\mu$m.

The solid particles preferably have an average diameter of about 15 to about 200 $\mu$m and more preferred from about 15 to about 60 $\mu$m.

In this case the solid particles are also small enough to be injected through a cannula of an injection syringe to the desired site.

Particles having the diameters specified above can also not be identified by touch as a single foreign body in or under the skin.

The solid particles preferably have such a diameter that they are not washed away through lymph tracts or other tissue tracts from the site to which they have been brought.

If the solid particles do not have a spherical form, then the diameter as used in the present documents refers to the greatest diameter of the smallest cross sectional area.

Due to the form, surface and size of the particles used they are not detected by the endogenous macrophages as foreign bodies so that no defensive reactions take place.

The particles having a spherical form or a spherical like form have the advantage that they form a closely packed arrangement at the site where they have been brought.

The solid particles used according to the present invention consist of an inert, histocompatible material. Such material can, for instance, be glass which is present in the form of glass beads or glass pellets having a smooth and smoothed off surface.

The solid particles used according to the present invention consist preferably of a polymer and in particular of a completely cured and fully polymerised polymer so that no remaining monomers, which may be toxic or may cause cancer, are incorporated into the body of the treated patient.

In principle, it is possible to use any inert histocompatible polymer for producing the polymer particles used according to the present invention. Preferably polymethacrylates and in particular polymethylmethacrylate (PMMA) are used as polymers.

Fully polymerised PMMA is histocompatible and can be incorporated in the human body without fear so that it can be considered as chemically and physically inert.

Due to this reason said polymer has already been used for manufacturing implants, for instance for the plastic covering of bone defects in the face and in the cranium or as an arthroplasty. Said polymer is also being used for manufacturing artificial teeth, as suture material and for manufacturing intraocular lenses and dialysis membranes.

To inject the solid particles or polymer particles, respectively, used according to the present invention as an implant in or under the skin, said particles are preferably suspended in a kind of suspending agent. For instance, water, alcohols, in particular ethyl alcohol, as well as mixtures thereof can be used as suspending agents.

The suspending agents used according to the present invention perferably contain a tenside, for instance Tween 80, since such a tenside changes the surface tension of water so that the solid particles and in particular the polymer particles float better.

The mixing ratio of the components of the suspending agent can be chosen according to the needs and in particular according to the size of the syringe used for the injection. A suitable mixture consists of 0.5 ml ethylalcohol, 0.5 ml Tween 80 and 9 ml water. The term "Tween" is a trademark of ICI Americas Inc. Under this nomination polyoxyethylenderivatives of sorbitanesters are distributed. Tween 80 is a polyethoxysorbitanoleate. It is not only possible to use the mentioned Tween type (Tween 80) but also other Tween types for the purposes of the present invention.

For the application or injection, respectively, of the solid particles used according to the present invention, the particles are suspended or slurried, respectively, in a fluid inert medium. It has been found advantageous to choose a ratio of two volume parts of the suspending agent and one volume part of the solid particles or polymer particles, respectively.

Preferably a gel which is known per se and is degraded within the body, for instance on the basis of gelatine, is used as a suspending agent.

By using a suspending agent it is easier to inject the solid particles as used according to the present invention with the help of an injection syringe for instance intracutenously. It is for instance possible to use a 20 G to 27 G cannula for such an injection.

To investigate which tissue reactions take place after the exogenous materials used according to the present invention have been injected, animal experiments have been performed.

For these experiments, PMMA-beads with a smooth, smoothed off surface having different diameters, for instance from 40 to 80 $\mu$m as well as from 15 to 60 $\mu$m, have been used. A mixture out of 0.5 ml ethylalcohol, 0.5 ml Tween and 9 ml water has been used as suspending agent. Such PMMA-beads or pellets, respectively, are known per se and are commercially available.

The suspending agent, which prevents the small beads from settling in the injection syringe due to gravitation such that an injection would be impossible, are mixed with the PMMA-beads before the injection in a ratio of about 1 volume part beads and 2 volume parts suspending agent.

The alloplastic implant according to the invention was injected into male wistar rats, weighing 200 to 250 g and being completely anaesthetised with Nembutal, at four places in an amount of 0.5 ml with the help of a 20 G cannula intracutenously into the peritoneal skin. It was the intention to use the peritoneal skin of the animals since it is much softer and more flexible than the skin on the backside. After the injection, small weals formed at the injection site due to the injected volume. This, however, was also the case when the suspending agent was injected alone.

The alloplastic implant of the present invention was injected into 39 animals. At days 3, 6, 9, 12, 15, 21 and 28 as well as 8, 12, 16, 20, 24 and 28 weeks after the injection three of the test animals were sacrificed. The peritoneal skin was then shaved with the help of a depilatory cream. At the injection site the beads, which were still visible but did not project anymore, were cut out together with a part of the peritoneal skin and investigated.

The results of the microscopic and macroscopic investigations performed can be summarised as follows.

None of the test animals died within the test time of 28 weeks. After the injection no defensive reactions or inflamations, respectively, were observed which were greater than those which are caused by an injury (insertion of the cannula). Such reactions were also not observed later on. No tumors could be found, neither in the area of the injection nor in the complete organism. No pathological changes of the peritoneal skin could be observed from the outside. After a couple of days the fur started growing again. The lymph tracts and the lymph nodules in the vicinity were without any pathological findings.

Monocytes migrate during the first three days after the injection of the PMMA-beads used into the area of the injection. Then a differentiation of the monocytes takes place. The different forms of said differentiation can be recognised after about 6 d after the application of the foreign bodies. It is possible to recognise macrophages, foreign body-giant cells and fibrocytes. Said process of differentiation lasts until about the 16th week after the implant of the invention has been injected. The process of differentiation is however, limited mainly to the fibrocytes which, after a further transformation to fibrinfibers, shield the PMMA-beads against the animal body.

Thereby a certain physical stability towards the interior and the exterior is imparted to the accumulation of balls.

Due to the size and the physical stability of the PMMA-beads they cannot be phagocytised or lysed, respectively. In order to "remove" the foreign body the animal body can only fibriotically wall off said foreign bodies. Such a process takes place with almost any foreign body which cannot be destroyed by the animal body.

The fibrotic growth of connective tissue is a natural reaction to the lesion of the tissue caused by the injection cannula. Said fibrotic reaction breaks down completely already after a couple of weeks due to the smooth surface and the chemical inertness of the PMMA-beads. From then on said beads remain in the tissue without reaction.

It can therefore be summarised that the PMMA-beads, which have been inserted into the body, are encapsulated by a delicate capsel of connective tissue or are embedded into connective-tissue fibers, respectively, and remain stationary in the tissue.

The use of the above described suspending agent is by the way not mandatory since the above described PMMA-beads can be injected also without a suspending agent into the body.

In order to investigate the reaction of the test animals with respect to the incorporation of PMMA-beads without a suspending agent the peritoneal skin of the test animals was opened by a stab incision. Than the PMMA-powder was strawn into the opening. The wound was than closed by a single button suture.

The same course of reaction as in the case of the above described tests could be observed. A delicate connective-tissue capsel was formed which enclosed the PMMA-beads.

It should, however, be advisable to use a suspending agent if an intracutenous or subcutenous injection under the skin of a human being shall be performed since in this case the implant of the invention can be more easily injected with a syringe.

If it is desired that the beads used float better in the suspending agent it is also possible to replace the tenside mentioned in the beginning by charging the beads in the same sense. Than they repell mutually and float better in the medium of the suspending agent which can consist in this case exclusively of water, alcohol or a mixture thereof.

For charging the PMMA-beads in the same sense said beads can be treated in such a way that the beads already completely cured are molten once again at the surface and than charged in an electric field.

I claim:

1. In an alloplastic implant including a histocompatible solid, the improvement comprising said solid being in a powder form and composed of loose solid particles, at least substantially entirely all of said particles each having a smooth surface free from corners and edges, wherein said particles are introduced into the body as loose particles and remain as loose particles to form substantially the entire said implant and wherein said solid particles have a diameter such that they cannot be washed away via lymph tracts or other tissue tracts from the implantation site.

2. Implant according to claim 1, wherein the solid particles are dynamically balanced and have at least one of an elliptical or spherical form.

3. Implant according to claim 1, wherein the solid particles have a diameter of at least 10 $\mu$m and an average diameter of 15 to 200 $\mu$m.

4. Implant according to claim 1, wherein the solid is a cured polymer.

5. Implant according to claim 4, wherein the polymer is a polymethacrylate.

6. Implant according to claim 1, wherein the solid particles are present in a physiologically acceptable suspending agent.

7. Implant according to claim 6, wherein the suspending agent is a gelatine degradable in the body.

8. Implant according to claim 6, wherein the suspending agent is liquid and consists of at least one of water or an alcohol.

9. Implant according to claim 3, wherein the solid particles have a diameter of 15–60 $\mu$m.

10. Implant according to claim 5, wherein said polymer is a polymethylmethacrylate.

11. Implant according to claim 8, wherein said suspending agent is ethylalcohol.

12. Implant according to claim 8, wherein said suspending agent is admixed with a tenside.

13. In an alloplastic implant including a histocompatible solid, the improvement comprising said solid being in a powder form and composed of loose solid particles, at least substantially entirely all of said particles each having a smooth surface free from corners and edges wherein the solid particles have a diameter of at least 10 $\mu$m and an average diameter of 15 to 200 $\mu$m such that said particles which remain as loose particles to form substantially the entire said implant cannot be washed away via lymph tracts or other tissue tracts from the implantation site.

14. In the alloplastic implant of claim 1, wherein said solid particles are non-porous beads.

15. In the alloplastic implant of claim 13, wherein said solid particles are non-porous beads.

* * * * *

UNITED STATES PATENT AND TRADEMARK OFFICE
Certificate

Patent No. 5,344,452                                                                 Patented: September 6, 1994

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Martin Lemperle, Frankfurt, Fed. Rep. Of Germany; and Gottfried Lemperle, La Jolla, CA.

Signed and Sealed this Thirty-first Day of August 2004.

CORRINE M. MCDERMOTT
*Supervisory Patent Examiner*
Art Unit 3738